(12) United States Patent
Patwardhan et al.

(10) Patent No.: US 11,206,967 B2
(45) Date of Patent: Dec. 28, 2021

(54) COMPACT BINOCULAR IMAGE CAPTURE DEVICE

(71) Applicant: INTUITIVE SURGICAL OPERATIONS, INC., Sunnyvale, CA (US)

(72) Inventors: Viraj A. Patwardhan, Milpitas, CA (US); John A Barton, Mountain View, CA (US); Mathew Clopp, Santa Clara, CA (US); John E. Sell, Los Altos, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 0 days.

(21) Appl. No.: 16/787,447

(22) Filed: Feb. 11, 2020

(65) Prior Publication Data

US 2020/0214545 A1 Jul. 9, 2020

Related U.S. Application Data

(63) Continuation of application No. 16/316,696, filed as application No. PCT/US2017/032716 on May 15, 2017, now Pat. No. 10,575,714.
(Continued)

(51) Int. Cl.
*H04N 7/18* (2006.01)
*A61B 1/00* (2006.01)
(Continued)

(52) U.S. Cl.
CPC ...... *A61B 1/00193* (2013.01); *A61B 1/00009* (2013.01); *A61B 1/0011* (2013.01);
(Continued)

(58) Field of Classification Search
CPC ... A61B 1/00193; A61B 90/361; A61B 34/30; A61B 34/35; A61B 1/00009;
(Continued)

(56) References Cited

U.S. PATENT DOCUMENTS 6,493,608 B1 12/2002 Niemeyer et al.
6,671,581 B2 12/2003 Niemeyer et al.
(Continued)

FOREIGN PATENT DOCUMENTS

CN 105280580 A 1/2016
JP 2000229065 A * 8/2000
(Continued)

OTHER PUBLICATIONS

Dankelman et al, Current Technology on Minimally Invasive Surgery and Interventional Techniques (Year: 2011).*
(Continued)

*Primary Examiner* — Shan E Elahi
(74) *Attorney, Agent, or Firm* — Haynes and Boone, LLP

(57) ABSTRACT

An image capture device includes a plurality of stacked ceramic circuit boards, an image sensor, signal conditioning electronics, and a connector. Each ceramic circuit board is parallel and directly coupled to at least one other circuit board. The image sensor is mounted to a first ceramic circuit board. The signal conditioning electronics are mounted to one or more of the stacked ceramic circuit boards and are coupled to receive electrical signals generated by the image sensor. The image capture device is enclosed by a shaft and the stacked ceramic circuit boards are stacked along a length of the shaft. The connector is mounted to a second ceramic circuit board that is on an opposite side of the plurality of stacked ceramic circuit boards from the first ceramic circuit
(Continued)

board. The connector is mounted to a side of the second ceramic circuit board facing away from the first ceramic circuit board.

19 Claims, 13 Drawing Sheets

Related U.S. Application Data

(60) Provisional application No. 62/362,224, filed on Jul. 14, 2016.

(51) Int. Cl.
| | | |
|---|---|---|
| A61B 1/313 | (2006.01) | |
| A61B 1/05 | (2006.01) | |
| A61B 90/00 | (2016.01) | |
| A61B 34/30 | (2016.02) | |
| A61B 34/35 | (2016.02) | |
| A61B 1/12 | (2006.01) | |
| A61B 90/30 | (2016.02) | |

(52) U.S. Cl.
CPC .......... *A61B 1/00149* (2013.01); *A61B 1/051* (2013.01); *A61B 1/128* (2013.01); *A61B 1/3132* (2013.01); *A61B 34/30* (2016.02); *A61B 34/35* (2016.02); *A61B 90/361* (2016.02); *A61B 1/00004* (2013.01); *A61B 2034/301* (2016.02); *A61B 2090/0813* (2016.02); *A61B 2090/309* (2016.02); *A61B 2090/371* (2016.02)

(58) Field of Classification Search
CPC ....... A61B 1/128; A61B 1/0011; A61B 1/051; A61B 1/00149; A61B 1/3132; A61B 2090/0813; A61B 2090/309; A61B 1/00004; A61B 2090/371; A61B 2034/301; A61B 1/05; G03B 35/10
USPC .......................................................... 348/48
See application file for complete search history.

(56) References Cited

U.S. PATENT DOCUMENTS

| | | | |
|---|---|---|---|
| 6,817,974 | B2 | 11/2004 | Cooper et al. |
| 8,599,242 | B2 | 12/2013 | Suh et al. |
| 2008/0045789 | A1 | 2/2008 | Sawachi |
| 2009/0109429 | A1* | 4/2009 | Scott ................ G01N 29/043 356/237.1 |
| 2010/0007701 | A1* | 1/2010 | Lee ............................ B41J 2/14 347/50 |
| 2010/0097057 | A1* | 4/2010 | Karpen ............. G01N 21/8806 324/238 |
| 2010/0261961 | A1 | 10/2010 | Scott et al. |
| 2011/0166706 | A1 | 7/2011 | Prisco et al. |
| 2011/0298704 | A1 | 12/2011 | Krah |
| 2011/0316994 | A1 | 12/2011 | Lemchen |
| 2012/0213436 | A1 | 8/2012 | Grindstaff et al. |
| 2013/0188058 | A1* | 7/2013 | Nguyen ................ G01J 5/0265 348/164 |
| 2014/0005485 | A1 | 1/2014 | Tesar et al. |
| 2014/0077833 | A1* | 3/2014 | Lee .......................... G01R 3/00 324/756.03 |
| 2014/0370650 | A1* | 12/2014 | Moslehi ................. H01L 31/18 438/98 |
| 2015/0141759 | A1 | 5/2015 | Charles et al. |
| 2015/0312457 | A1 | 10/2015 | Kojima |
| 2019/0150716 | A1 | 5/2019 | Patwardhan et al. |

FOREIGN PATENT DOCUMENTS

| | | | |
|---|---|---|---|
| JP | 2007007429 | A | 1/2007 |
| JP | 2015062555 | A | 4/2015 |
| WO | WO-0156458 | A1 | 8/2001 |
| WO | WO-2011060296 | A2 | 5/2011 |
| WO | WO-2014020360 | A1 | 2/2014 |
| WO | WO-2014203604 | A1 | 12/2014 |

OTHER PUBLICATIONS

Tobergte et al, An approach to ulta-tightly coupled data fusion for handheld input devices in robotic surgery (Year: 2011).*
Miyashita et al, Solid Imaging Instrument, English translation of JP 2000229065 A (Year: 2000).*
International Preliminary Report on Patentability for Application No. PCT/US2017/032716, dated Jan. 24, 2019, 10 pages.
International Search Report and Written Opinion for Application No. PCT/US2017/032716, dated Jul. 14, 2017, 15 pages.
Lee J., et al., "Modeling and Control of Robotic Surgical Platform for Single-port Access Surgery," IEEE/RSJ International Conference on Intelligent Robots and Systems, Sep. 2014, pp. 3489-3495.
Monnich H., et al., "A Supervision System for the Intuitive Usage of a Telemanipulated Surgical Robotic Setup," IEEE International Conference on Robotics and Biomimetics, Dec. 2011, pp. 449-454.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.
Zinchenko K., et al., "A Study on Speech Recognition Control for a Surgical Robot," IEEE Transactions on Industrial Informatics, Apr. 2017, vol. 13 (2), pp. 607-615.
Extended European Search Report for Application No. 17828110.1, dated Feb. 20, 2020, 9 pages.

* cited by examiner

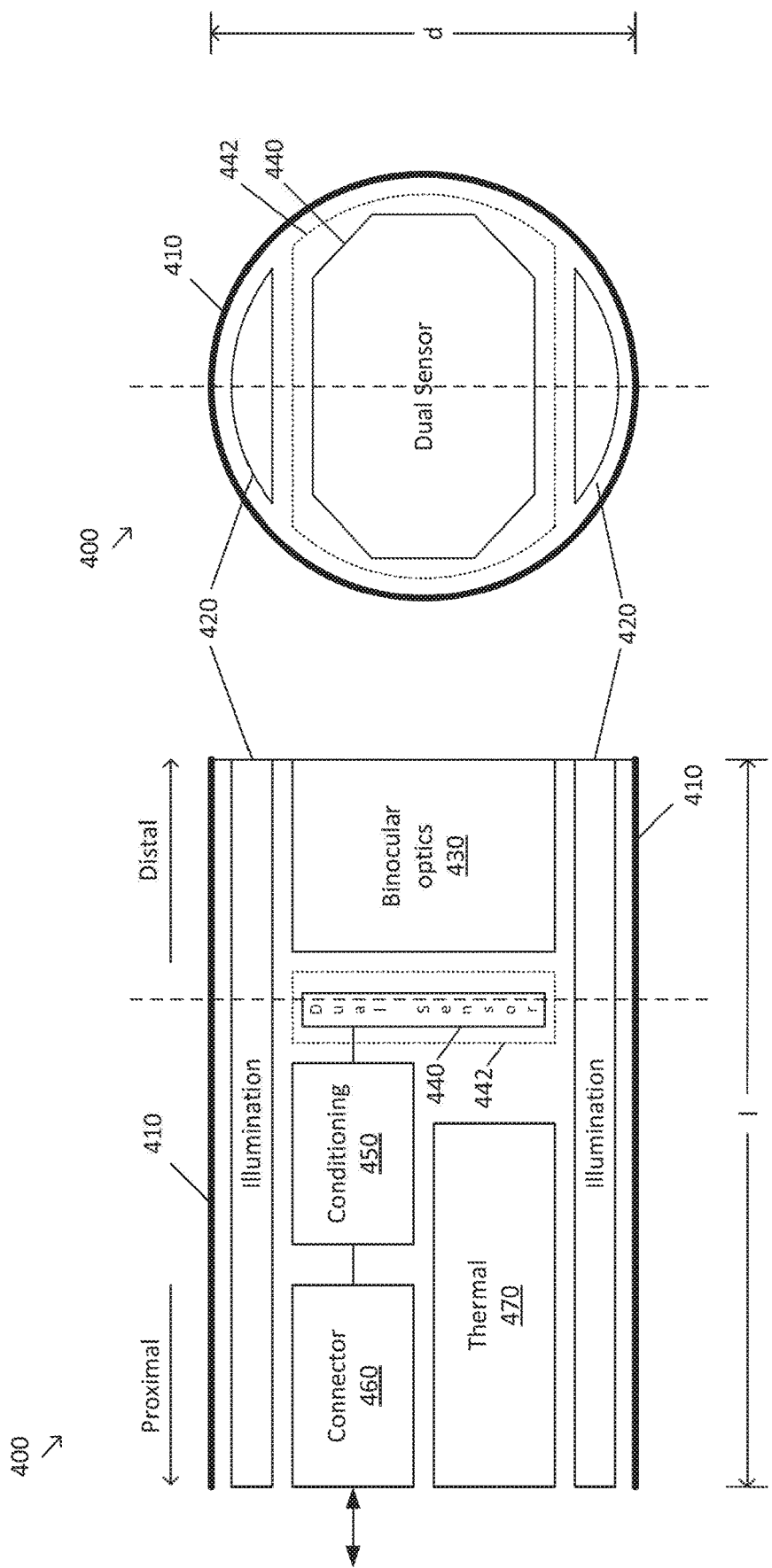

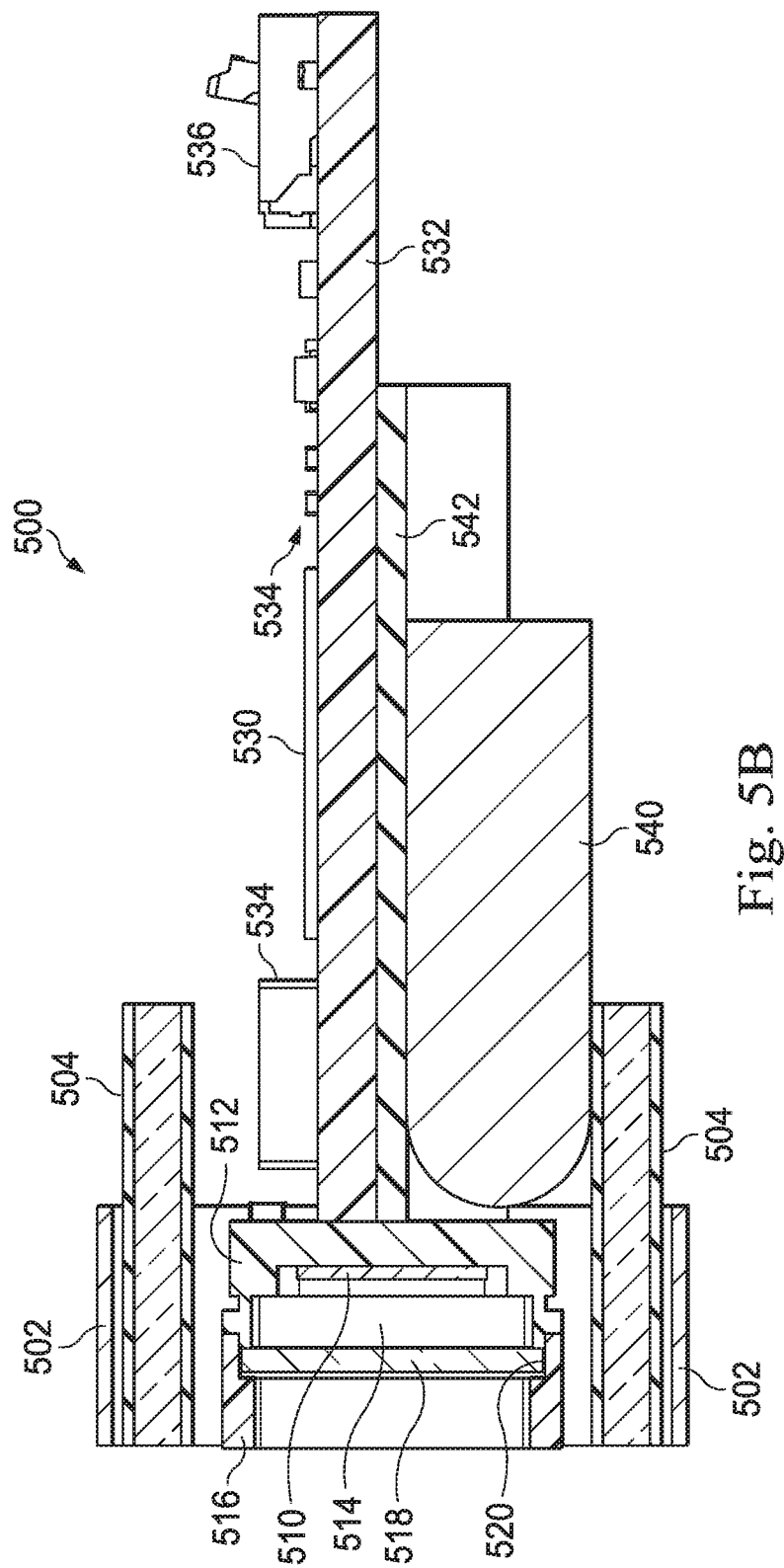

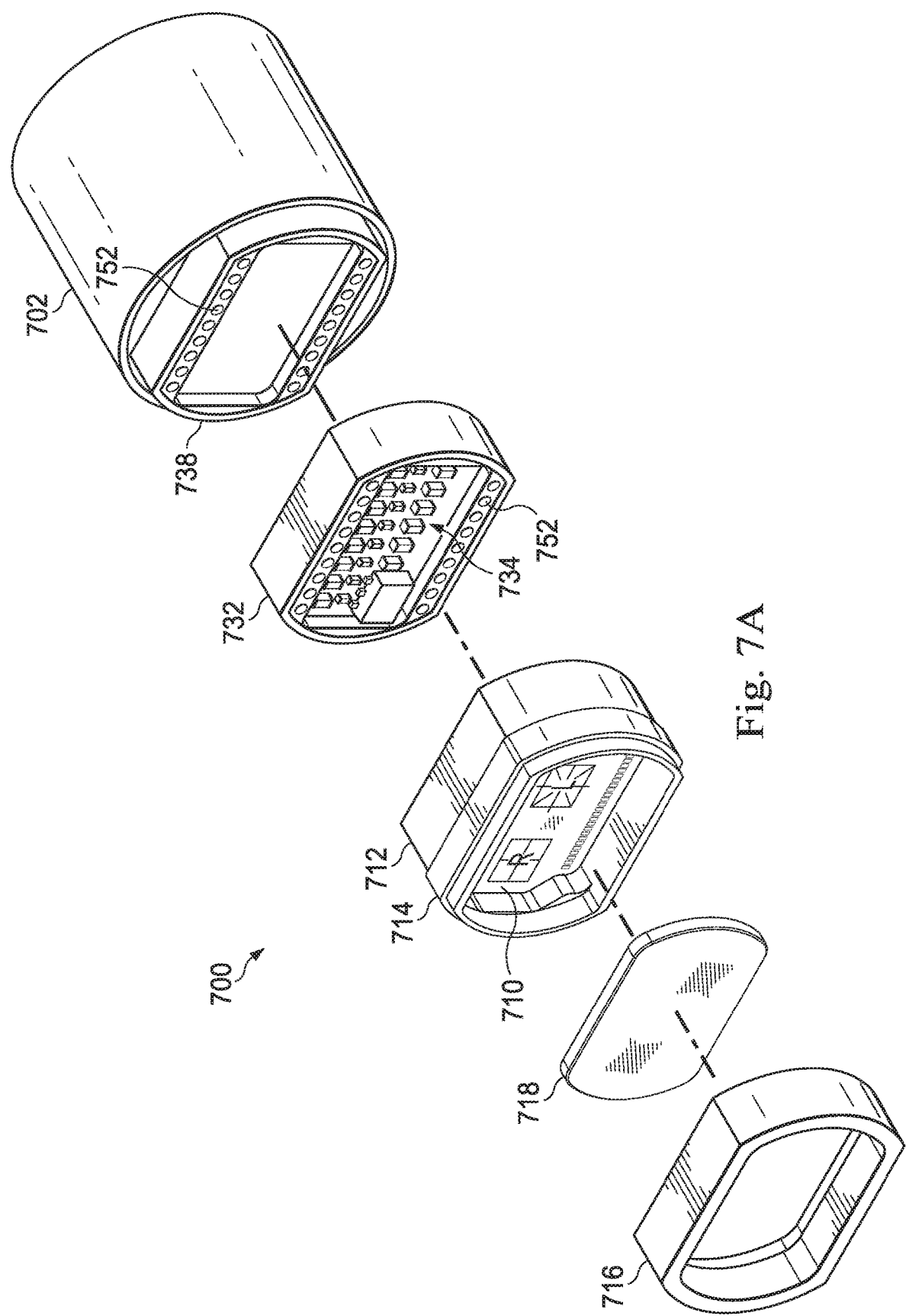

COMPACT BINOCULAR IMAGE CAPTURE DEVICE

PRIORITY

This patent application is the continuation application of U.S. patent application Ser. No. 16/316,696, filed Jan. 10, 2019, which is the U.S. national phase of International Application No. PCT/US2017/032716, filed May 15, 2017, which designated the U.S. and claims priority to and the benefit of the filing date of U.S. Provisional Patent Application 62/362,224, entitled "COMPACT BINOCULAR IMAGE CAPTURE DEVICE," filed Jul. 14, 2016, all of which are incorporated by reference herein in their entirety.

TECHNICAL FIELD

The present disclosure is directed to image capturing devices for conducting an image-guided procedure and more particularly to a compact binocular image capturing device for conducting an image-guided procedure.

BACKGROUND

Medical robotic systems such as teleoperational systems used in performing minimally invasive surgical procedures offer many benefits over traditional open surgery techniques, including less pain, shorter hospital stays, quicker return to normal activities, minimal scarring, reduced recovery time, and less injury to tissue. Consequently, demand for such medical teleoperational systems is strong and growing.

Examples of medical teleoperational systems include the da Vinci® Surgical System and the da Vinci® S™ Surgical System from Intuitive Surgical, Inc., of Sunnyvale, Calif. Each of these systems includes a surgeon's consoler a patient-side cart, a high performance three-dimensional ("3-D") vision system, and Intuitive Surgical's proprietary EndoWrist® articulating instruments, which are modeled after the human wrist. When added to the motions of manipulators holding the surgical instruments, these articulating instruments allow at least six degrees of freedom of motion to their end effectors, which is comparable to or even greater than the natural motions of open surgery. During the performance of a medical procedure, it is useful to view two or three dimensional live images of the surgical site captured by an image capturing device. The image capturing device is sterilized by an autoclave cleaning process prior to being used during the medical procedure.

Accordingly, it would be advantageous to provide an image capturing device that supports binocular imaging in a compact form factor that is compatible with autoclave cleaning.

SUMMARY

The embodiments of the invention are best summarized by the claims that follow the description.

In some examples, a binocular image capture device may include a plurality of stacked circuit boards, a front-facing dual image sensor mounted to a first circuit board of the plurality of stacked circuit boards, and signal conditioning electronics mounted to one or more of the plurality of stacked circuit boards and coupled to receive electrical signals generated by the dual image sensor. The dual image sensor is enclosed in a hermetic housing.

In some examples, a binocular image capture device may include a first circuit board and a second circuit board arranged in a tombstone configuration such that the second circuit board is mounted to first circuit board at a perpendicular angle, a front-facing dual image sensor mounted to the first circuit board, and signal conditioning electronics mounted to the second circuit board and coupled to receive electrical signals generated by the dual image sensor. The dual image sensor is enclosed in a hermetic housing.

In some examples, a method for assembling a binocular image capture device may include securing a dual image sensor to a first circuit board, securing a signal conditioning electronics to one or more second circuit boards, stacking the first circuit board and the one or more second circuit boards to electrically couple the dual image sensor and the signal conditioning electronics, and sealing the dual image sensor in an autoclave-tolerant hermetic housing.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTION OF THE DRAWINGS

FIGS. 4A and 4B are simplified diagram of a binocular image capturing device with a front-facing sensor according to some embodiments.

FIGS. 5A and 5B are simplified diagrams of a binocular image capture device in a tombstone configuration according to some embodiments.

FIGS. 7A-E are simplified diagrams of a binocular image capture device in a stacked configuration according to some embodiments.

DETAILED DESCRIPTION

Figure 1:
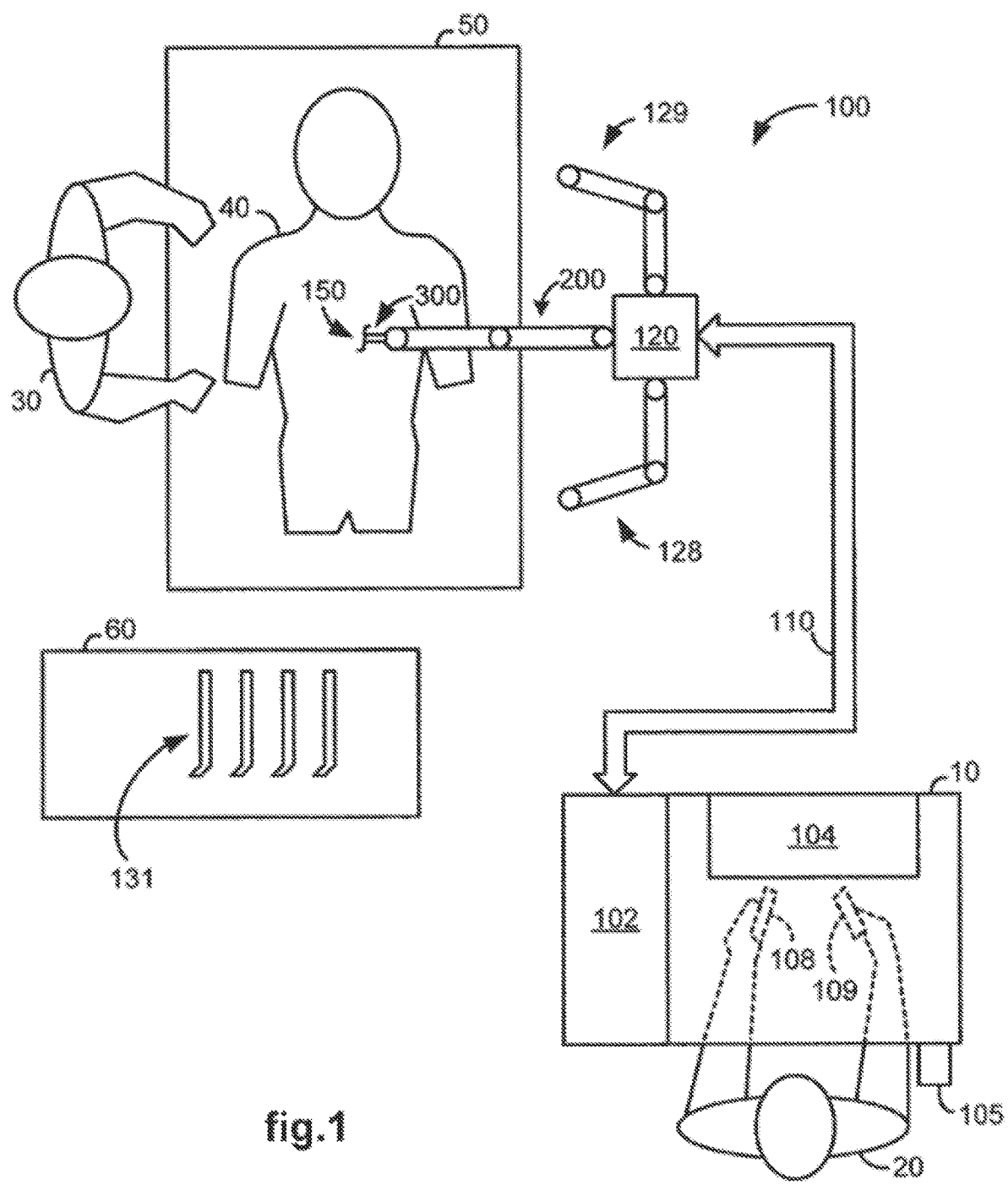
FIG. 1 is a simplified diagram of an operating room employing a medical teleoperational system with a bundled unit of medical devices according to some embodiments.

FIG. 1 illustrates, as an example, a top view of an operating room in which a medical teleoperational system 100 is being utilized by a Surgeon 20 for performing a medical procedure on a Patient 40 who is lying down on an operating table 50. One or more Assistants 30 may be positioned near the Patient 40 to assist in the procedure while the Surgeon 20 performs the procedure teleoperatively by manipulating control devices 108, 109 on a surgeon console 10.

In the present example, a bundled unit 300 of medical devices is inserted through a single entry port 150 into the Patient 40. The bundled unit 300 may be used in a single-port system. Although the entry port 150 is a minimally invasive incision in the present example, in the performance of other medical procedures, it may instead be a natural body orifice. The bundled unit 300 is held and manipulated by a teleoperational arm assembly 200 (also "arm 200"). Although only one teleoperational arm assembly is used in the present example, the medical teleoperational system 100 is equipped with additional teleoperational arm assemblies 128, 129 which are swung out of the way during the performance of the present medical procedure, because they are not being used.

The console 10 includes a 3-D monitor 104 for displaying a 3-D image of a surgical site to the Surgeon, left and right manipulatable control devices 108, 109, a foot pedal 105, and a processor 102. The control devices 108, 109 may include any one or more of a variety of input devices such as joysticks, gloves, trigger-guns, hand-operated controllers, or the like. The processor 102 may be a dedicated computer integrated into the console 10 or positioned next or near to it, or it may comprise a number of processing or controller components that are distributed in a distributed processing fashion throughout the system 100.

The console 10 is usually located in the same room as the Patient so that the Surgeon may directly monitor the procedure, is physically available if necessary, and is able to speak to the Assistant(s) directly rather than over the telephone or other communication medium. However, it will be understood that the Surgeon can also be located in a different room, a completely different building, or other remote location from the Patient allowing for remote surgical procedures.

Figure 3:
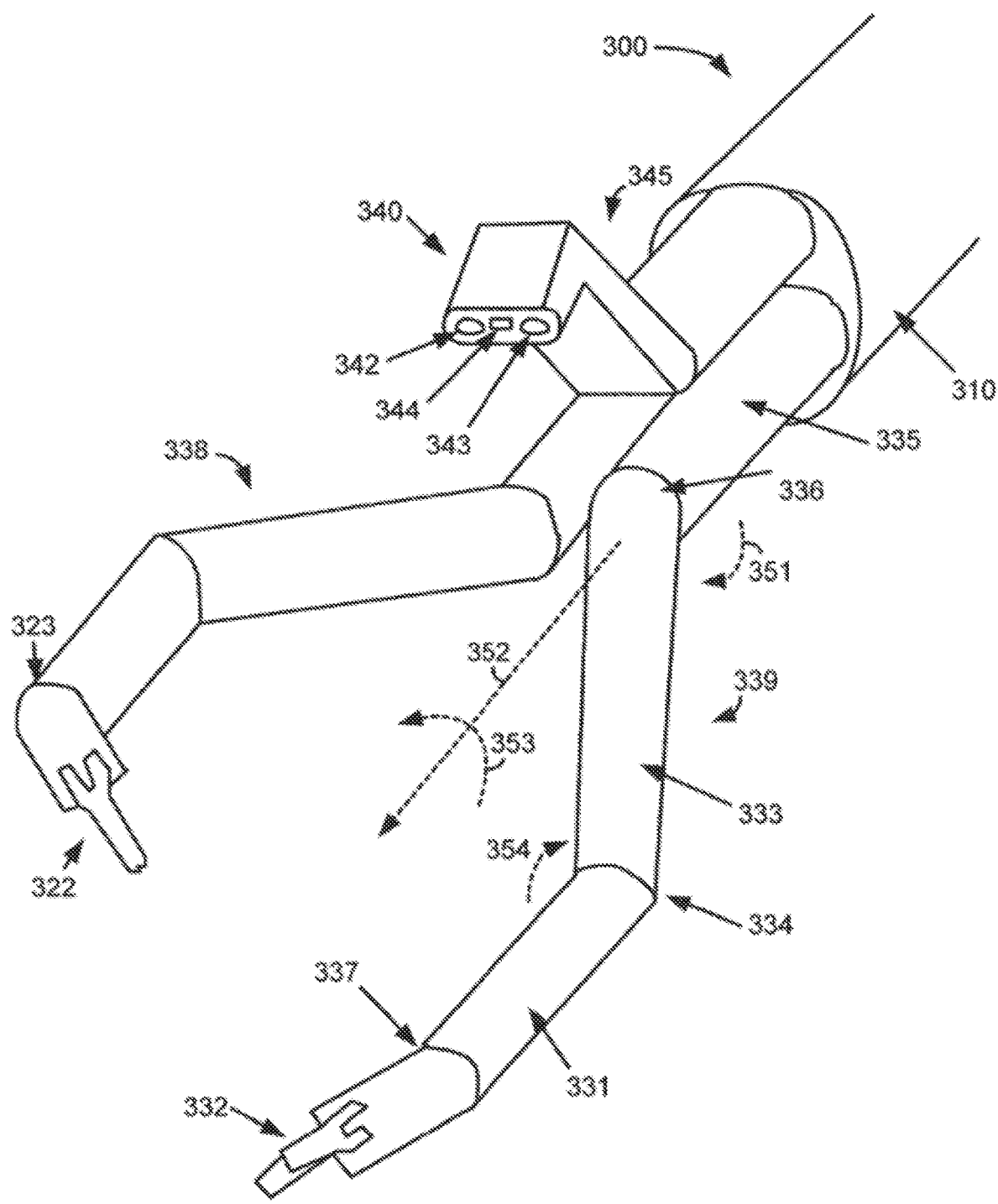
FIG. 3 is a simplified diagram of a distal end of a bundled unit of medical devices according to some embodiments.

As shown in FIG. 3, the bundled unit 300 may include two surgical instruments or tools 338, 339 and an image capturing device 340 (also "image capturing unit 340"). Each of the surgical tools 338, 339 is associated with one of the control devices 108, 109. The Surgeon performs a medical procedure by manipulating the control devices 108, 109 so that the processor 102 causes corresponding movement of their respectively associated surgical tools 338, 339, while the Surgeon views the surgical site in 3-D on the console monitor 104 as it is captured by the image capturing device 140.

Preferably, control devices 108, 109 will be provided with at least the same degrees of freedom as their associated tools 338, 339 to provide the Surgeon with telepresence, or the perception that the control devices 108, 109 are integral with the tools 338, 339 so that the Surgeon has a strong sense of directly controlling the tools 338, 339.

Preferably, the monitor 104 is positioned near the Surgeon's hands so that it will display a projected image that is oriented so that the Surgeon feels that he or she is actually looking directly down onto the operating site. To that end, images of the tools 338, 339 preferably appear to be located substantially where the Surgeon's hands are located.

In addition, the real-time image is preferably projected into a perspective image such that the Surgeon can manipulate the end effectors 322, 332 of the tools 338, 339 through their corresponding control devices 108, 109 as if viewing the workspace in substantially true presence. By true presence, it is meant that the presentation of an image is a true perspective image simulating the viewpoint of an operator that is physically manipulating the tools 338, 339. Thus, the processor 102 transforms the coordinates of the tools 338, 339 to a perceived position so that the perspective image is the image that one would see if the image capturing device 140 was located directly behind the tools 338, 339.

The processor 102 performs various functions in the system 100. One important function that it performs is to translate and transfer the mechanical motion of control devices 108, 109 to the teleoperational arm assembly 200 through control signals over bus 110 so that the Surgeon can effectively manipulate the tools 338, 339.

Although described as a processor, it is to be appreciated that the processor 102 may be implemented in practice by any combination of hardware, software and firmware. Also, its functions as described herein may be performed by one unit or divided up among different components, each of which may be implemented in turn by any combination of hardware, software and firmware. Further, although being shown as part of or being physically adjacent to the console 10, the processor 102 may also comprise a number of subunits distributed throughout the system such as in printed circuit boards installed in the patient side cart 120 and/or the teleoperational arm assemblies 128, 129, 200, as well as, or alternatively to, the console 10.

For additional details on the construction and operation of various aspects of a medical teleoperational system such as described herein, see, e.g., commonly owned U.S. Pat. No. 6,493,608 "Aspects of a Control System of a Minimally Invasive Surgical Apparatus," and commonly owned U.S. Pat. No. 6,671,581 "Camera Referenced Control in a Minimally Invasive Surgical Apparatus," which are incorporated herein by reference.

Figure 2:
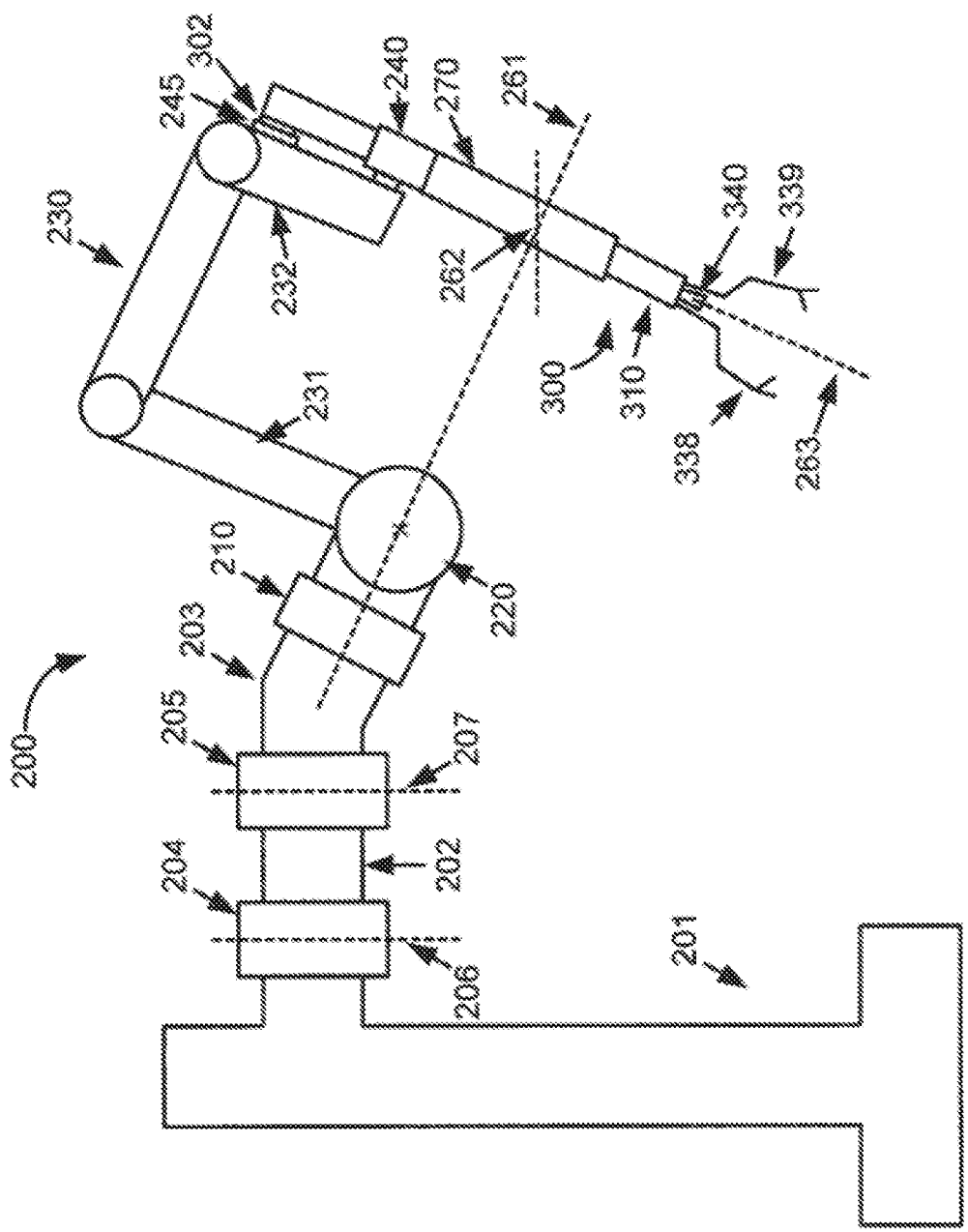
FIG. 2 is a simplified diagram of a teleoperational and assembly holding a bundled unit of medical devices according to some embodiments.

FIG. 2 illustrates, as an example, a simplified side view (not necessarily to scale or complete) of the teleoperational arm assembly 200 which is holding the bundled unit 300 of medical devices. A tool guide 270 is inserted through the minimally invasive incision comprising the entry port 150 in the Patient in this example, and coupled to the teleoperational arm assembly 200 by a guide holder 240. The bundled unit 300 may then be inserted into the Patient through the tool guide 270. The teleoperational arm assembly 200 is mechanically supported by a base 201 of the patient side cart 120.

Links 202, 203 are coupled together and to the base 201 through horizontal setup joints 204, 205. The setup joints 204, 205 in this example are passive joints that allow manual positioning of the arm 200 when their brakes are released. For example, setup joint 204 allows link 202 to be manually rotated about axis 206, and setup joint 205 allows link 203 to be manually rotated about axis 207.

Although only two links and two setup joints are shown in this example, more or fewer of each may be used as appropriate in this and other teleoperational arm assemblies in conjunction with the present invention. For example, although setup joints 204, 205 are useful for horizontal positioning of the arm 200, additional setup joints may be included and useful for limited vertical and angular positioning of the arm 200. For major vertical positioning of the arm 200, however, the arm 200 may also be slidably moved along the vertical axis of the base 201 and locked in position.

The teleoperational arm assembly 200 also includes two active joints and a number of gears driven by motors. A yaw joint 210 allows arm section 230 to rotate around an axis 261, and a pitch joint 220 allows arm section 230 to rotate about an axis perpendicular to that of axis 261 and orthogonal to the plane of the drawing. An interface 302 comprises mating parts on the carriage 245 and the proximal end of the bundled unit 300 such as motor driven gears that actuate movement of the surgical tools 338, 339 and image capturing unit 340 through conventional joints, cable and pulley systems.

The arm section 230 is configured so that sections 231, 232 are always parallel to each other as the pitch joint 220 is rotated by its motor. As a consequence, the bundled unit 300 may be controllably moved by driving the yaw and pitch motors so as to pivot about the pivot point 262, which is generally located through manual positioning of the setup joints 204, 205 so as to be at the point of entry into the Patient. In addition, the bundled unit 300 is coupled to a carriage 245 on the arm section 230 which in turn is coupled to a linear drive mechanism to extend or retract the bundled unit 300 along its insertion axis 263.

Although each of the yaw joint 210, pitch joint 220 and motor driven gears in the carriage 245 is controlled by an individual joint or gear controller, the controllers may be controlled by a common master/slave control system so that the medical devices of the bundled unit 300 may be controlled through user (e.g., Surgeon or operator) manipulation of its associated control device.

FIG. 3 illustrates, as an example, a perspective view of a distal end of the bundled unit 300. The bundled unit 300 includes removable surgical tools 338, 339 for performing a medical procedure and a removable image capturing unit 340 for viewing the procedure at a surgical site within a patient. Each of the tools 338, 339 and image capturing unit 340 extends through a separate lumen formed in an inner core of the bundled unit 300. Replacement of one or both of the surgical tools 338, 339 during or in preparation for performing a medical procedure may then be accomplished by the Assistant removing the tool that is no longer needed from its lumen and replacing it with a substitute tool 131 from a tray 60 by inserting the substitute tool 131 in the vacated lumen. Alternatively, if unused lumens are available, an additional tool may be inserted through one of those available lumens without removing any other tools already in place.

The image capturing device 340 preferably includes a stereoscopic pair of cameras 342, 343 (and/or a single binocular camera) for three-dimensional imaging of the surgical site and an illuminating device 344 such as a light emitting diode (LED) or a fiber optics bundle carrying light from an external source, to enhance visibility of objects in the captured images. Auxiliary image capturing units, such as an ultrasound probe, may also be provided in available lumens of the bundled unit 300 for "seeing" into anatomic structures for surgical or diagnostic purposes.

In some embodiments, an overtube 310 is also included in the bundled unit 300 for protecting its inner core and the medical devices (i.e., surgical tools and image capturing units) inserted therethrough. The overtube 310 may be rigid. Alternatively, it may be formed of flexible material or comprise actively and/or passively bendable sections so that the bundled unit 300 may conform to the shapes of body lumens as it moves therethrough to a surgical site within a patient.

The surgical tools 338, 339 each have a controllably extendable, rotatable, and bendable arm to which their respective end effectors 322, 332 are coupled to by wrist mechanisms 323, 337. For example, the arm of the surgical tool 339 comprises three links 331, 333, 335 coupled by distal joints 334, 336. The proximal link 335 is controllably extendable and retractable along an insertion axis 352 (which is preferably parallel to the insertion axis 263 of the bundled unit 300), and is controllably rotatable (as shown by rotation angle 353) about the insertion axis 352. The middle link 333, on the other hand, is controllably bendable by distal joint 336 relative to the link 335 (as shown by bend angle 351), and the distal link 331 is coupled to the links 333, 335 and bendable by distal joint 334 so that its bend angle 354 is in an opposite direction as that of the link 333 and consequently, keeps links 331, 335 in parallel alignment.

The arm of the surgical tool 338 is similarly constructed as that of the surgical tool 339. Additional details for one example of the wrist mechanisms 323, 337 are provided in commonly owned U.S. Pat. No. 6,817,974 "Surgical Tool Having Positively Positionable Tendon-Actuated Multi-Disk Wrist Joint," which is incorporated herein by this reference.

The image capturing device 340 also has a controllably extendable, rotatable, and bendable arm 345 that facilitates at least insertion/retraction of the image capturing unit 340 along its insertion axis (which may be parallel to the insertion axis 263 of the bundled unit 300) and pitch motion in order to achieve a sufficient elevation of the image capturing device 340 "above" the surgical tools 338, 339 so as to properly view them during a surgical procedure. Additional degrees of freedom, such as roll angular movement of the image capturing device 340 about its insertion axis, may also be provided in order to facilitate additional positioning and orientation capabilities for the image capturing device 340. For enhanced maneuverability, the image capturing arm 345 may also be bendable such as the controllably bendable, rotatable, and extendable arms of the surgical tools 338, 339.

FIGS. 4A and 4B are simplified diagrams of a binocular image capturing device 400 with a front-facing sensor according to some embodiments. According to some embodiments consistent with FIGS. 1-3, image capturing device 400 may be used to implement image capturing device 340 of bundled unit 300. According to some embodiments, binocular image capturing device 400 may be used in systems other than bundled unit 300. In particular, image capturing device 400 is well-suited for imaging applications that demand small feature size, ruggedness, and ability to withstand autoclaving. For example, binocular image capture device 400 may be used in medical instruments such as medical teleoperational systems, and/or handheld endoscopes. While binocular image capture device 400 may be particularly well-suited for medical imaging applications, binocular image capture device 400 may also be used in general imaging applications, such as photography and/or video applications of mobile devices.

According to some embodiments, binocular image capture device 400 includes one or more features that facilitate a small feature size and/or a compact design. In some examples, the diameter 'd' of binocular image capture device 400 may be less than 10 mm. In some examples, the aspect ratio (i.e., the ratio between the length 'l' and the diameter 'd') of binocular image capture device 400 may be less than 10:1.

As depicted in FIGS. 4A and 4B, binocular image capturing device 400 acquires binocular images from a perspective of forward-looking out of a distal end of an elongate device. In some embodiments, the elongate device may be an endoscope capable of being inserted into an anatomical port and/or anatomical passageway for acquiring images during a medical procedure. Consistent with such embodiments, binocular image capturing device 400 may be positioned at the distal tip of an endoscope.

A shaft 410 fully or partly encloses components of binocular image capturing device 400. In some examples, shaft 410 may correspond to an 8.8 mm endoscope shaft, in which case the diameter 'd' of shaft 410 is 8.8 mm. More generally, the diameter 'd' of shaft 410 is sufficiently small to accommodate insertion/retraction of binocular image capturing device 400 through anatomical ports and/or anatomical passageways. According to some embodiments, shaft 410 may be formed using a rigid tube. In some embodiments, shaft 410 may be flexible. Although depicted as having a circular cross-section, it is to be understood that the cross-section of shaft 410 may be ellipsoidal, polygonal, and/or any other suitable shape. In some examples, the diameter 'd' and/or the shape of shaft 410 may vary along the length of shaft 410. Although components of binocular image capturing device 400 are generally disposed within shaft 410, some components may protrude from the sides of shaft 410 and/or out of the distal end of shaft 410.

An optional illumination module 420 provides illumination from the distal end of binocular image capturing device 400. In some embodiments, binocular image capturing device 400 is used to capture scenes with little or no ambient illumination, such as interior anatomical cavities and/or passageways. Consequently, illumination module 420 serves as the primary source of illumination to the scene in support of image acquisition. In some embodiments, illumination module 420 may include one or more illumination sources, such as light emitting diodes (LEDs). In some examples, the illumination source may include a ring of LEDs to increase the brightness and uniformity of the illumination. In some embodiments, the illumination source may be external to illumination module 420, in which case illumination module may include passive optical components, such as fiber optic lines, lenses, mirrors, and/or the like. For example, illumination module 420 may include one or more fiber optic lines to route illumination received from the proximal end of binocular image capture device 400 around the components binocular image capture device 400 and out the distal end. As depicted in FIGS. 4A and 4B, illumination module 420 includes two such fiber optic lines disposed on opposite sides of shaft 410 to provide uniform illumination intensity to the scene.

Binocular optics module 430 receives illumination (i.e., light and/or other electromagnetic signals) from the scene and projects a pair of images onto a dual image sensor 440. Binocular optics module 430 may include one or more lenses, mirrors, apertures, filters, prisms, polarizers, and/or the like to achieve desired image characteristics (e.g., focal length and/or spectral characteristics). One or more components of binocular optics module 430 may be adjustable so as to vary the image characteristics (e.g., to vary the focal length).

Dual image sensor 440 generally includes any device suitable for converting the pair of projected images from binocular optics module 430 into analog and/or digital electrical signals that retain at least a portion of the information contained in the projected images. According to some examples, dual image sensor 440 may include a charge coupled device (CCD) sensor, active pixel sensor, complementary metal oxide semiconductor (CMOS) sensor, N-type metal oxide semiconductor (NMOS) sensor and/or the like. According to some embodiments, dual image sensor 440 may include a single monolithic sensor with dual active areas, and/or may include a plurality of discrete sensors.

In general, it is desirable for the active area of an image sensor, such as dual image sensor 440, to be as large as possible to improve image quality. For instance, relative to a small image sensor, a large image sensor may have more pixels for improved resolution and/or larger pixels for improved sensitivity. However, because binocular image capture device 400 has a small diameter 'd' (e.g., 10 mm or less), the space available for an image sensor is generally constrained, particularly in the direction of the diameter. One way to increase the area of an image sensor while satisfying the space constraints of binocular image capture device 400 is to mount the image sensor in a sideways-facing configuration. In the sideways-facing configuration, one edge of the image sensor lies along the length of binocular image capture device 400 and therefore is not subject to the diameter constraints. However, the sideways-facing configuration is problematic for several reasons. First, in order to project images onto a sideways-facing image sensor, binocular optics module 430 is tasked with redirecting light from the distal end of image capture device 400 by 90 degrees. This generally increases the complexity and/or cost of the binocular optics module 430 and may degrade image quality. Second, although in some instances a sideways-facing image sensor may be used for monocular imaging applications, the sideways-facing image sensor is even more challenging to integrate in binocular imaging applications. Especially given the space constraints of binocular image capture device 400, projecting a pair of images onto a sideways-facing image sensor may involve substantial additional complexity and cost. Thus, a sideways-facing image sensor may not be well-suited for use in binocular image capture device 400.

In order to address these challenges, dual image sensor 440 of binocular image capture device 400 is configured as a front facing image sensor, with an active area that is oriented towards the distal end of binocular image capture device 400. In the front facing configuration, binocular optics module 430 may be simplified, cheaper, and/or more compact relative to a sideways-facing configuration because the projected images are not redirected by 90 degrees and because there is little additional complexity involved in binocular imaging applications relative to monocular imaging applications.

In order to increase the active area of dual image sensor 440 in the front-facing configuration while satisfying the diameter constraints of shaft 410, the shape of dual image sensor 440 may be adapted to conform to the cross-sectional shape of shaft 410. For example, when shaft 410 has a circular cross-section, an octagon shape conforms better to shaft 410 than a rectangular shape. Accordingly, dual image sensor 440 may have an octagonal shape, as may be formed by sawing or cleaving the corners off of a rectangular sensor.

In some embodiments, dual image sensor 440 may be disposed in a hermetic housing 442. Hermetic housing 442 protects dual image sensor 440 from moisture and/or other contaminants. Moreover, hermetic housing 442 is mechanically robust to the temperature cycles experienced during autoclave cleaning. Although hermetic housing 442 is depicted as encapsulating dual image sensor 440, it is to be understood that other components of binocular image capture device 400 may also be hermetically sealed in hermetic housing 442. Embodiments of hermetic housing 442 are described in greater detail below with reference to FIGS. 5-7.

In some examples, the electrical signals generated by dual image sensor 440 have a relatively small signal amplitude. In particular, due to their low amplitude, the electrical signals may not be suitable for transmission over long distances, e.g., from the distal end to the proximal end of a teleoperational arm assembly. Accordingly, dual image sensor is electrically coupled to a conditioning module 450, which receives the electrical signals generated by dual image sensor 440 and converts them for transmission. In some examples, conditioning module 450 may include signal conditioning electronics including one or more image signal processors (ISPs), amplifiers, analog to digital (A/D) converters, image encoders, and/or the like. In some examples, the output of conditioning module 450 may be a digital video signal feed. The digital video signal feed (or another signal representation of captured image data) is transmitted out of binocular image capture device 400 via a connector 460. In some examples, connector 460 is configured to transmit image data and to receive power and/or control signals.

To improve image quality, components of conditioning module 450 are generally positioned in close physical proximity to dual image sensor 440. This prevents or mitigates the degradation of the electrical signals generated by dual image sensor 440 over long transmission lines. This also facilitates a compact, simple, and robust design. In some examples, an image signal processor of conditioning module 450 may be disposed on the backside of dual image sensor 440 (i.e., a "flip-chip" configuration). In some examples, the image signal processor and dual image sensor 440 may be mounted on opposite sides of a circuit board such that electrical signals generated by dual image sensor 440 are routed a short distance through the circuit board (e.g., a few mm or less). In some examples, the image signal processor and/or other components of conditioning module 450 may be mounted in a "tombstone" configuration relative to dual image sensor 440, as described in greater detail below with reference to FIGS. 5 and 6. In some examples, conditioning module 450 may be mounted in a "stacked" configuration relative to dual image sensor 440, as described in greater detail below with reference to FIG. 7.

During operation, electronic components of binocular image capture device 400 (which may include various components of illumination module 420, dual image sensor 440, conditioning module 450, and/or connector 460) generate waste heat. A thermal management module 470 is optionally used to conduct the waste heat away from binocular image capture device 400 to prevent overheating. In some embodiments, thermal management module 470 may include a heat sink that is thermally coupled to one or more components of binocular image capture device 400. In some examples, the heat sink may be configured to conduct heat in a proximal direction away from binocular image capture device 400. In some examples, thermal management module 470 may include thermally conductive paste applied at various locations throughout binocular image capture device 400. However, in some embodiments, binocular image capture device 400 may not include thermal management module 470. Specifically, the compact design of binocular image capture device 400 may provide sufficient thermal conduction to prevent overheating without a dedicated thermal management module 470.

Figure 5A:
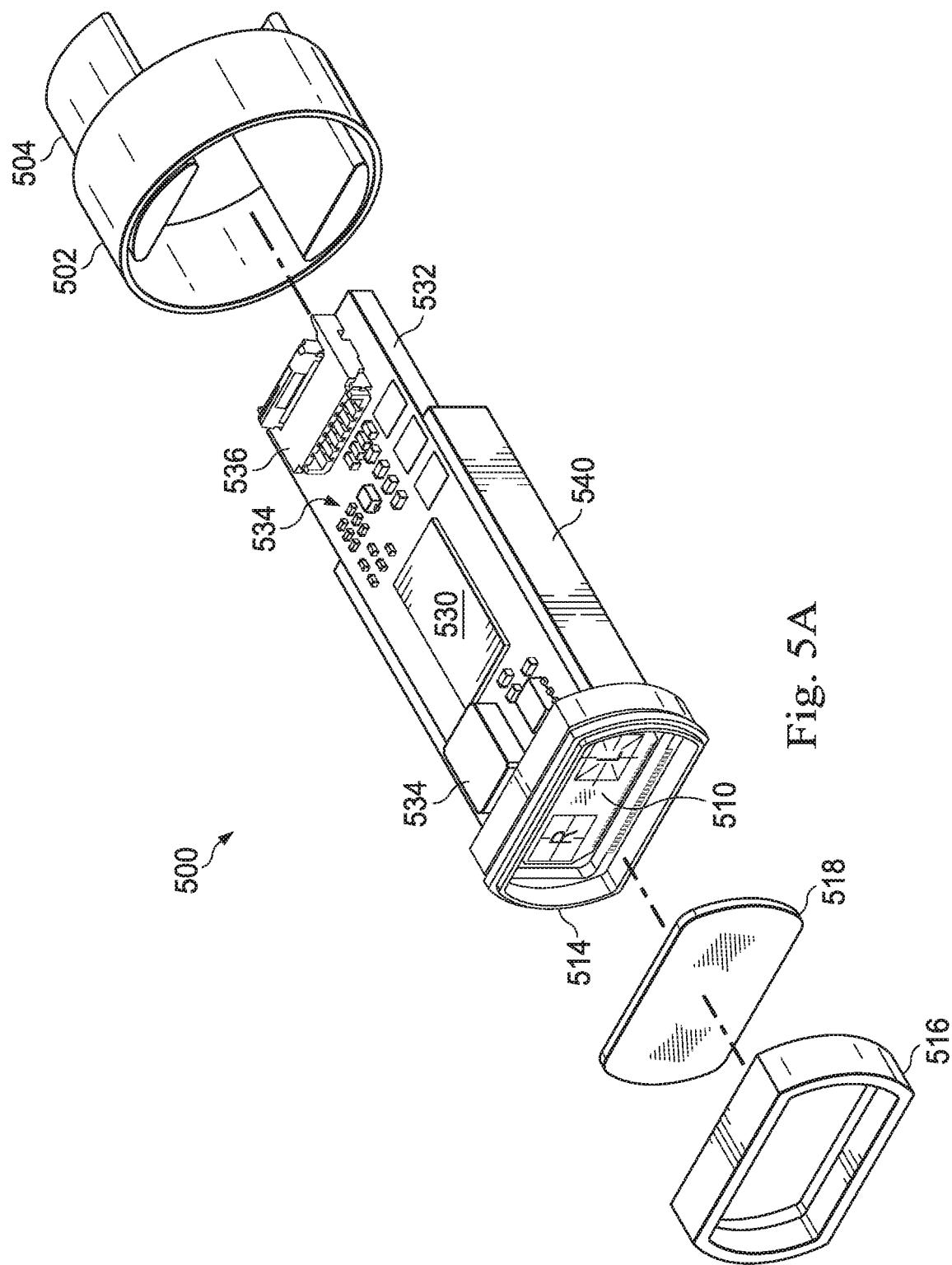

FIGS. 5A and 5B are simplified diagrams of a binocular image capture device 500 in a tombstone configuration according to some embodiments. In some embodiments consistent with FIGS. 1-4, binocular image capture device 500 may be used to implement at least some of the features of binocular image capture device 400.

Binocular image capture device 500 is fully or partially encased by an outer tube 502. A pair of fiber optic lines 504 are potted along upper and lower portions of outer tube 502. Although depicted as being located at a distal end of binocular image capture device 500 for clarity, outer tube 502 and/or fiber optic lines 504 may extend along the length of binocular image capture device 500. According to some embodiments consistent with FIGS. 1-4, outer tube 502 and fiber optic lines 504 may correspond to shaft 410 and illumination module 420, respectively.

A dual image sensor 510 with an octagonal in-plane shape is disposed in a forward-facing configuration oriented towards a distal end of binocular image capture device 500). Dual image sensor 510 is mounted on a circuit board 512.

According to some embodiments, dual image sensor 510 may be wire bonded to circuit board 512. In some examples, circuit board 512 may be a ceramic circuit board to provide a temperature and/or moisture resistant backing for dual image sensor 510. In some examples, circuit board 512 may be formed using another material with low (or zero) moisture penetration and/or high thermal conductivity.

A transition ring 514 is affixed to circuit board 512. In some examples, transition ring 514 may be a kovar ring that is affixed to circuit board 512 by brazing. In some examples, transition ring 514 may be formed using another material with a coefficient of thermal expansion (CTE) that matches the CTE of circuit board 512 and/or that is compatible with processes such as brazing, welding, gluing, and/or the like.

An optics housing 516 is affixed to transition ring 514. In some examples, optics housing 516 may be a stainless steel housing that is affixed to transition ring 514 by welding (e.g., laser welding). In some examples, the stainless steel housing may be formed using alloys such as 17-4 stainless steel and/or 440 stainless steel to match the CTE of circuit board 512, transition ring 514, and/or optical glass. In some examples, optics housing 516 may enclose binocular optics, such as binocular optics module 430. Binocular optics are not depicted in FIG. 5A of 5B for clarity, but may extend from the distal end of binocular image capture device in some embodiments. According to some embodiments, cover glass 518 may be affixed to a rim 520 of transition ring 514. For example, cover glass 518 may be affixed to transition ring 514 by glue.

According to some embodiments consistent with FIGS. 1-4, circuit board 512, ring 514, optics housing 516, and/or cover glass 518 may form a hermetically sealed chamber corresponding to hermetic housing 442. The hermetically sealed chamber encloses dual image sensor 510 and/or optical components (e.g., binocular optical module 430) disposed within optical housing 516. According to some embodiments, the hermetically sealed chamber may be filled with an inert gas (e.g., nitrogen) to reduce or prevent condensation or other contamination of dual image sensor 510 and/or the optical components contained in optical housing 516. Advantageously, the hermetically sealed chamber of binocular image capture device. 500 is formed using materials with matching CTE (e.g., ceramic circuit board 512, kovar transition ring 514, stainless steel optics housing 516, and optical glass used in binocular optics and/or cover glass 518) to reduce distortions and/or stress caused by thermal cycling during autoclave cleaning.

A circuit board 532 may include various signal conditioning electronics, such as an image signal processor 530, hosts electronics 534, and/or connector 536. Image signal processor 530 is coupled to receive electronic signals from dual image sensor 510 and generate digital image data based on the received electronic signals. The digital image data (e.g., a digital video feed) is output via connector 536. Electronics 534 may include one or more capacitors, resistors, diodes, oscillators, sensors (e.g. temperature sensors), and/or the like. In some examples, circuit board 532 may be a ceramic circuit board in order to improve tolerance to autoclave cleaning and/or harsh operating environments such as the human body. In some examples, circuit board 532 may be an FR-4 circuit board and/or any other suitable type of circuit board.

Circuit board 532 is mounted to circuit board 512 in a tombstone configuration. In the tombstone configuration, the edge of circuit board 532 abuts the backside of circuit board 512 at a right angle. As depicted in FIGS. 5A and 5B, circuit board 532 is mounted at approximately the vertical center of circuit board 512. In some examples, circuit board 532 may be rigidly affixed to circuit board 512. In some examples, circuit board 532 may be in direct contact with circuit board 512 and/or may be glued to circuit board 512. According to some embodiments consistent with FIGS. 1-4, the components mounted to circuit board 532 may correspond to conditioning module 450 and/or connector 460.

A heat sink 540 is coupled to circuit board 532 and/or circuit board 512 via a support member 542. Heat sink 540 configured to sink heat away from electronic components mounted to circuit board 532 and/or circuit board 512. Advantageously, the tombstone configuration provides access to a large surface area on the backside of circuit board 532 to maximize heat transfer from components mounted to the front side to heat sink 540. In some examples, heat sink 540 may be a copper heat pipe. In general, however, the CTE of copper does not match the CTE of a ceramic circuit board. Accordingly, support member 542 may be formed using a transition material that matches the CTE of ceramic, such as a Cu—Mo and/or Cu—W Consistent with such embodiments, support member 542 may be affixed to circuit board 532 and/or circuit board 512 by brazing. According to some embodiments consistent with FIGS. 1-4, heat sink 540 and/or support member 542 may correspond to thermal management module 470.

Figure 6A:
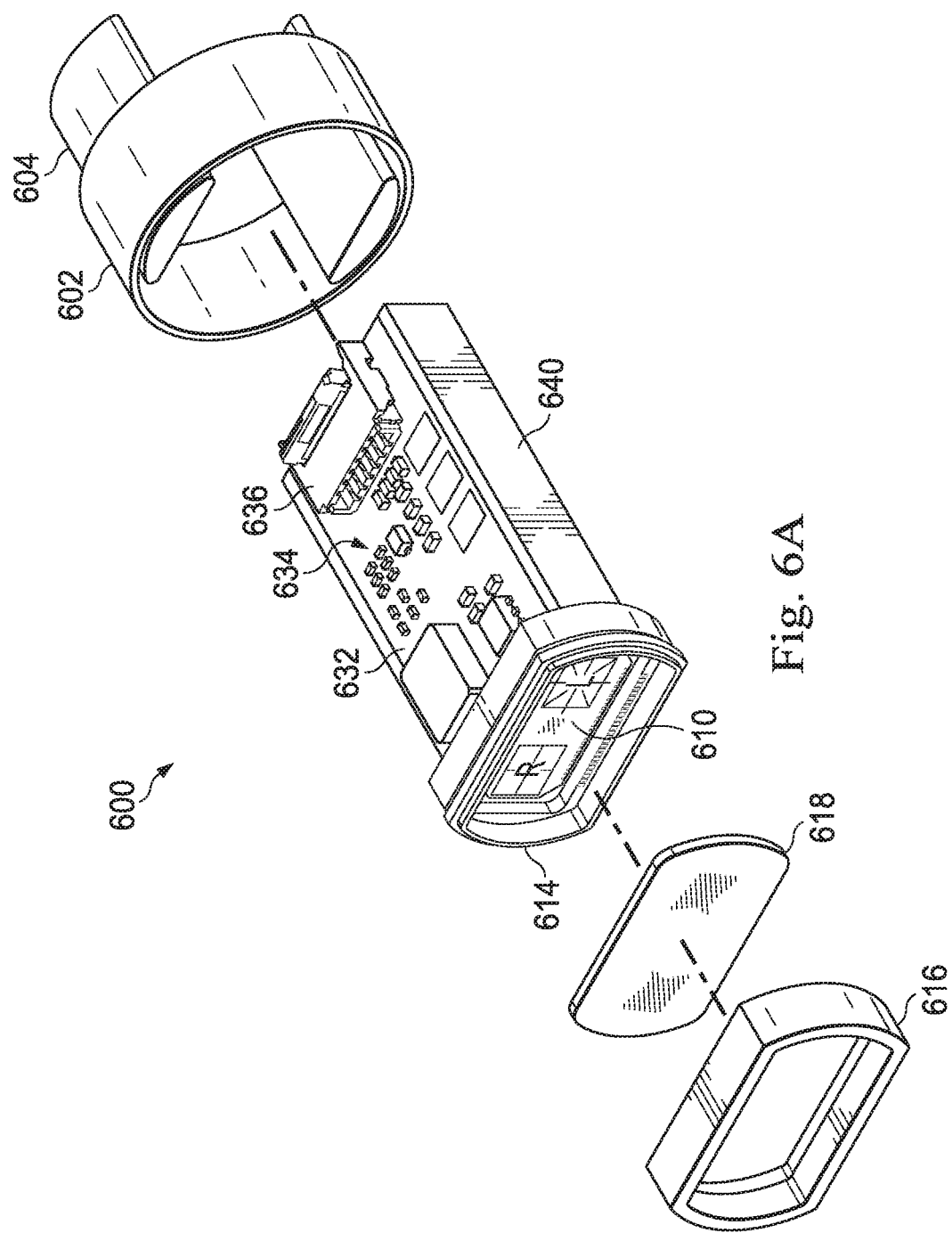
FIGS. 6A and 6B are simplified diagrams of a binocular image capture device in a tombstone configuration with a flip-chip image signal processor from an exploded perspective and a side view, respectively, according to some embodiments.
Figure 6B:
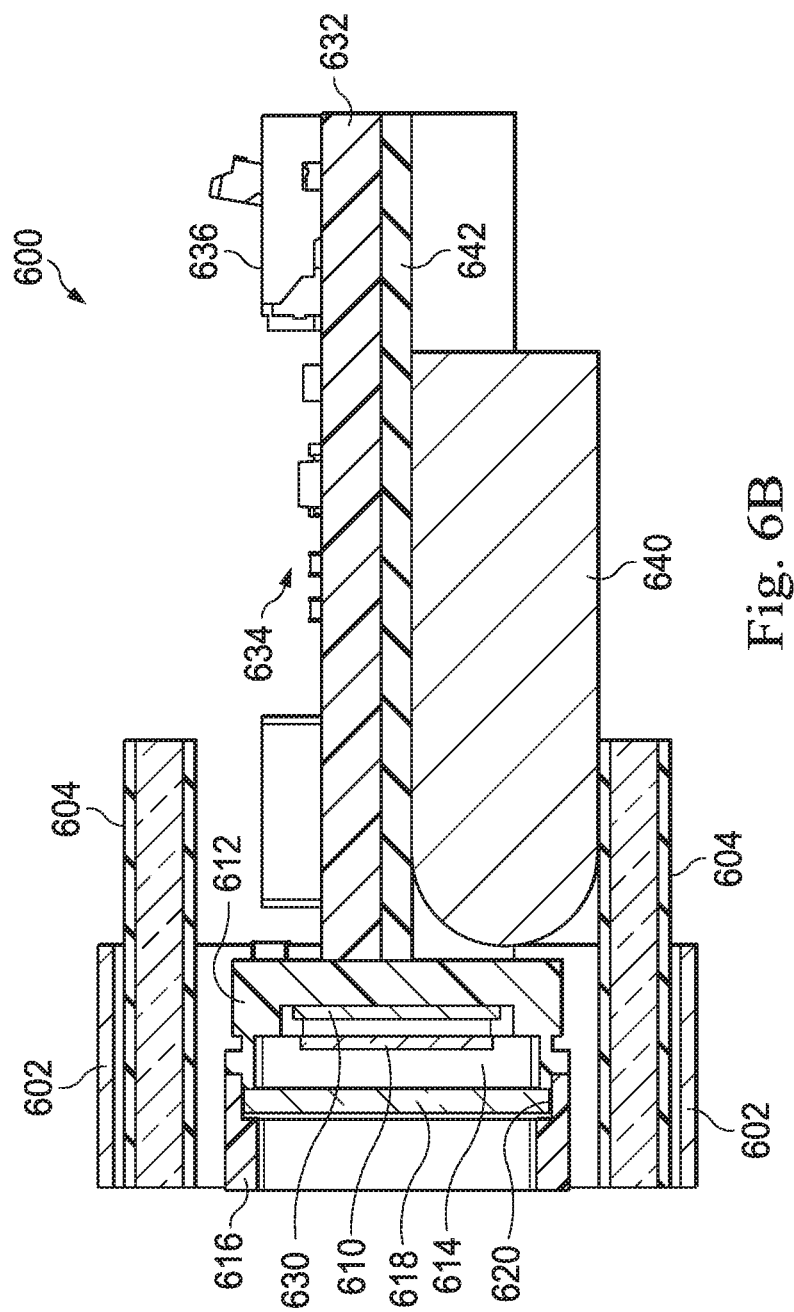

FIGS. 6A and 6B are simplified diagrams of a binocular image capture device 600 in a tombstone configuration with a flip-chip image signal processor according to some embodiments. According to some embodiments consistent with FIGS. 1-4, binocular image capture device may be used to implement at least some features of binocular image capture device 400.

Like binocular image capture device 500 of FIGS. 5A and 5B, binocular image capture device 600 includes a tube 602, fiber optic lines 604, a dual image sensor 610, a circuit board 612, a transition ring 614 with a rim 620, an optics housing 616, cover glass 618, an image signal processor 630, a circuit board 632, electronics 634, a connector 636, a heat sink 640, and a support member 642. In some examples, image signal processor 630, electronics 634, and/or connector 6236 may be used as signal conditioning electronics. These features generally correspond to similarly labeled features of FIGS. 5A and/or 5B.

Unlike image signal processor 530, which is mounted to circuit board 512, image signal processor 630 is disposed in a flip-chip configuration on the back side of dual image sensor 610. Advantageously, the flip-chip configuration of image signal processor 630 reduces the distance that electrical signals generated by dual image sensor 610 propagate to reach image signal processor 630, which improves image quality. Moreover, the flip-chip configuration reduces the number of discrete components because the dual image sensor 610 and image signal processor 630 are on the same chip. This reduces the complexity of binocular image capture device 600. Unlike other approaches to integrate dual image sensor 610 and image signal processor 630 on a single chip (e.g., a system-on-chip configuration with dual image sensor 610 and image signal processor 630 on the same side of a chip), the flip-chip configuration does not reduce the active area of dual image sensor 610.

FIGS. 7A-E are simplified diagrams of a binocular image capture device 700 in a stacked configuration according to some embodiments. According to some embodiments consistent with FIGS. 1-4, binocular image capture device may be used to implement at least some features of binocular image capture device 400.

Like binocular image capture devices 500 and 600, binocular image capture device 700 includes a tube 702, fiber optic lines 704, a dual image sensor 710, a circuit board 712, a transition ring 714 with a rim 720, an optics housing 716, cover glass 718, an image signal processor 730, a circuit board 732, electronics 734, a connector 736, a heat sink 740, and a support member 742. In some examples, image signal processor 730, electronics 734, and/or connector 736 may be used as signal conditioning electronics. These features generally correspond to similarly labeled features of FIGS. 5 and 6. As depicted in FIG. 7, image signal processor 730 is mounted to the back side of circuit board 712. FIG. 7 depicts several features that are not shown in FIGS. 5 and 6. For example, binocular image capture device 700 includes a heat sink extension 744 coupled to heat sink 740 by a threaded connector 746.

FIG. 7 depicts circuit boards 712 and 732 arranged in a stacked configuration. Optionally, the stacked configuration of circuit boards may include one or more additional circuit boards 750 to increase the total available circuit board area for components such as electronics 734 and/or connector 736. Advantageously, arranging the circuit boards in a stacked configuration may improve the compactness of binocular image capture device 700. Furthermore, although binocular image capture device 700 is depicted as including heat sink 740, the stacked configuration may offer sufficient heat conduction that heat sink 740 (and associated components such as support member 742, and heat sink extension 744) may be omitted.

To facilitate stacking, circuit boards 712, 732 and/or 750 may have the same or similar in-plane shape and dimensions. In some examples, circuit boards 712, 732, and/or 750 may have aligned bonding pads 752 to create one or more electrical contacts between adjacent circuit boards. That is, bonding pads on the front or distal side of a particular circuit board are lined up with bonding pads on the back or proximal side of a neighboring circuit board. In some embodiments, portions of the stacked circuit boards may be recessed relative to bonding pads 752 to form a gap between neighboring circuit boards in which to fit mounted components. Although the stack of circuit boards depicted in FIG. 7 includes three circuit boards 712, 732, and 750, it is to be understood that the stack of circuit boards may include any number of circuit boards.

According to some embodiments, adjacent circuit boards in the stack of circuit boards may be directly coupled to one another and/or coupled using an adhesive. Coupling between adjacent circuit boards facilitates heat transfer along the length of the stack of circuit boards, as one or more of the stacked circuit boards may not have a direct connection to heat sink 740. In some examples, electrical and/or mechanical contact between bonding pads 752 of adjacent circuit boards may be formed using solder, conductive epoxy, metal bonding (e.g. brazing, sintering, welding, and/or the like), anisotropic conductive film (ACF), anisotropic conductive paste (ACP), and/or the like.

Additionally or alternatively, adjacent circuit boards in the stack of circuit boards may be separated by gaps, such as air gaps. For example, a gap may be provided to accommodate large devices mounted to a circuit board, to allow the stack to bend, and/or the like. In this regard, the stacked configuration may include stacking circuit boards 712, 732 and/or 750 in any suitable arrangement with facing planar surfaces, with or without direct physical contact between adjacent circuit boards.

Figure 7B:
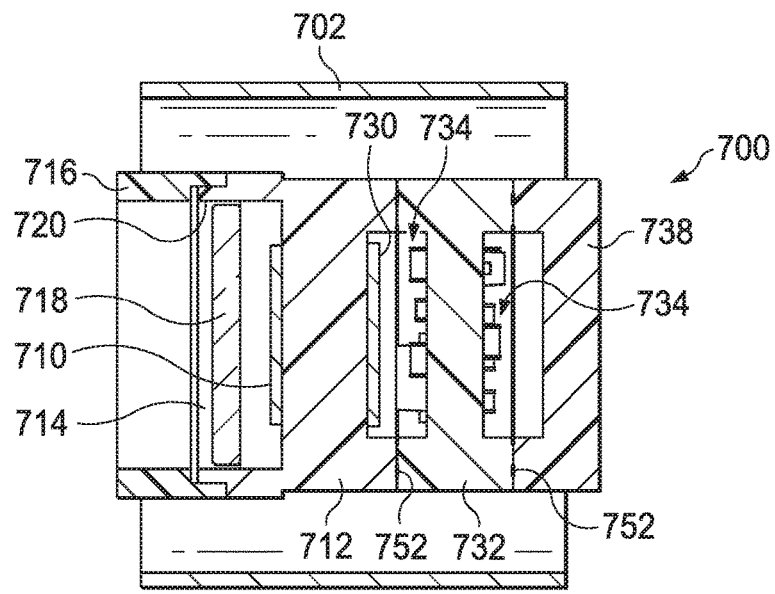
Figure 7D:
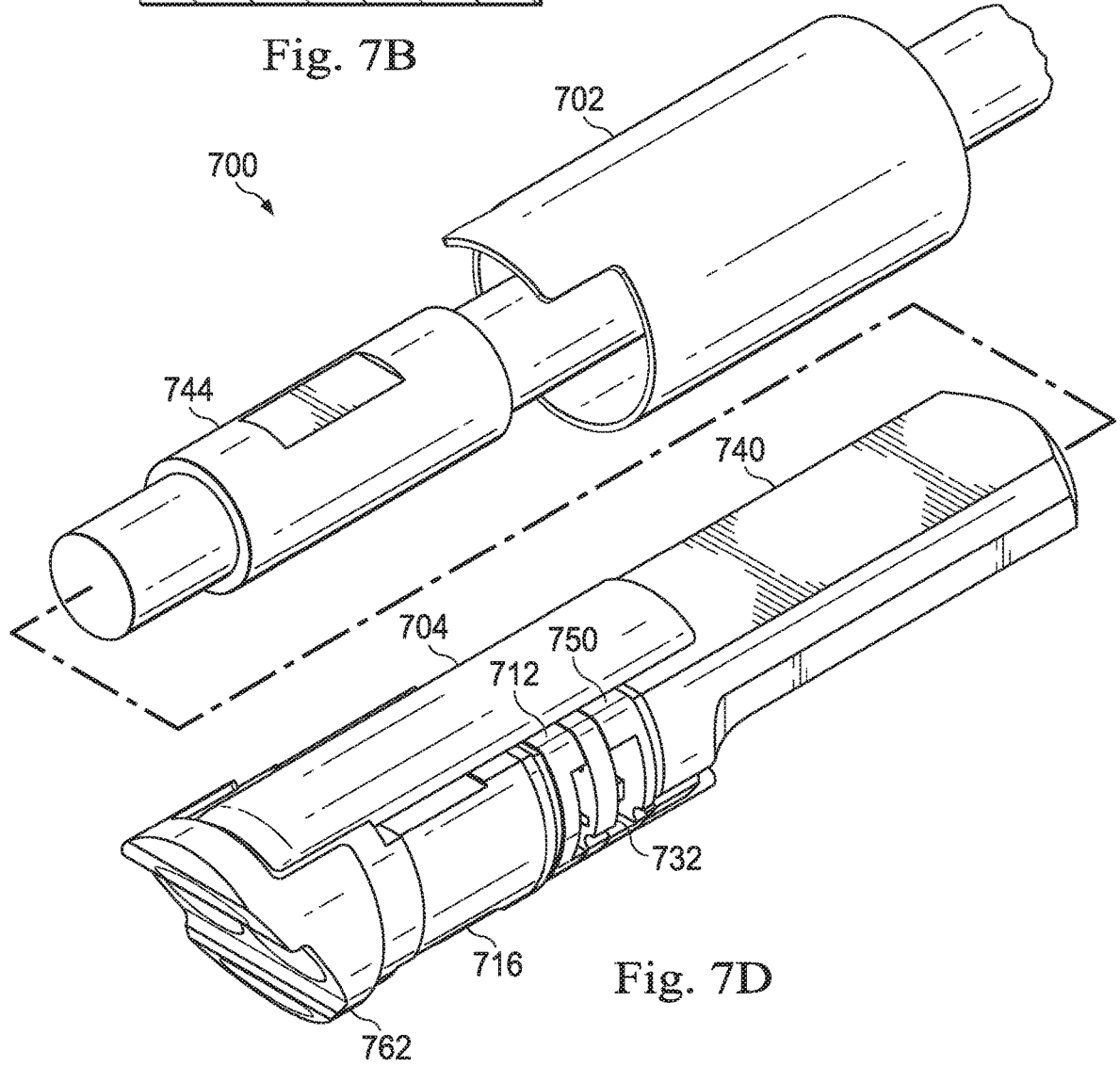
Figure 7C:
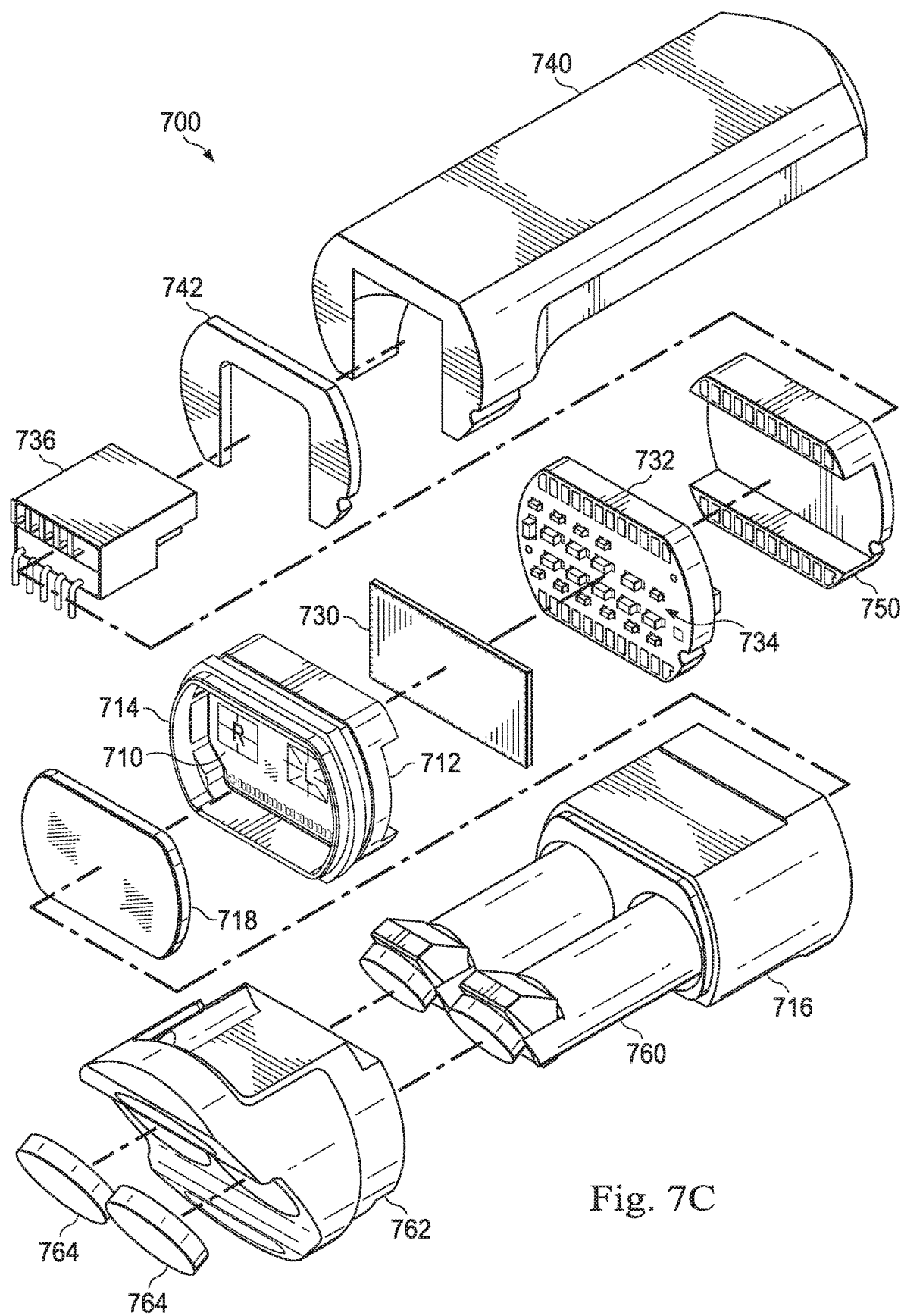
Figure 7E:
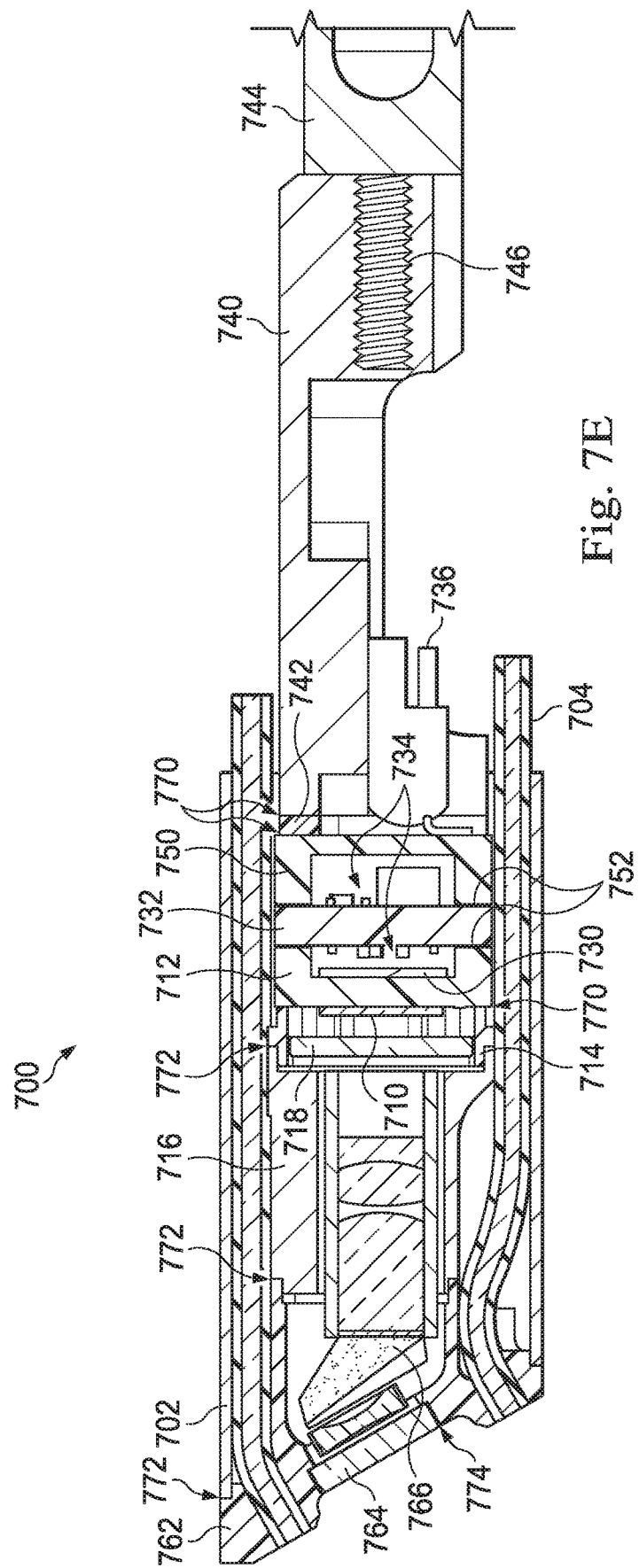

As depicted in FIGS. 7b and 7c, binocular image capture device 700 includes binocular optics 760, an endpiece 762, and windows 764. In some examples, windows 764 may be sapphire windows. According to some embodiments consistent with FIGS. 1-4, binocular optics 760, endpiece 762, and/or windows 764 may correspond to binocular optics module 430. Endpiece 762, optics housing 716, windows 764, cover glass 718, transition ring 714, and/or circuit board 712 form a hermetically sealed volume 766 that may be filled with an inert gas, such as nitrogen.

To facilitate hermeticity, mechanical integrity, and/or efficient heat transfer in binocular image capture device 700, abutting components of binocular image capture device 700 may be affixed using brazing (see, e.g., brazed interfaces 770) and/or welding (see, e.g., welded interfaces 772) techniques. In some examples, welded interfaces 772 may be laser welded. As depicted in FIG. 7c, examples of brazed interfaces 770 include the interfaces between heat sink 740 and support member 742; support member 742 and circuit board 750; and circuit board 712, and transition ring 714. Examples of welded interfaces 772 include the interfaces between transition ring 714 and optics housing 716; optics housing 716 and binocular optics 760; and between optics housing 716 and endpiece 762. The interface between endpiece 762 and windows 764 is a soldered interface 774. For example, windows 764 may be affixed to endpiece 762 using window solder. While specific embodiments have been described, it is to be understood that a variety of other techniques may be used to form interfaces between components, such as glass fritting, epoxy potting, sintering, adhesives, and/or the like.

Figure 8:
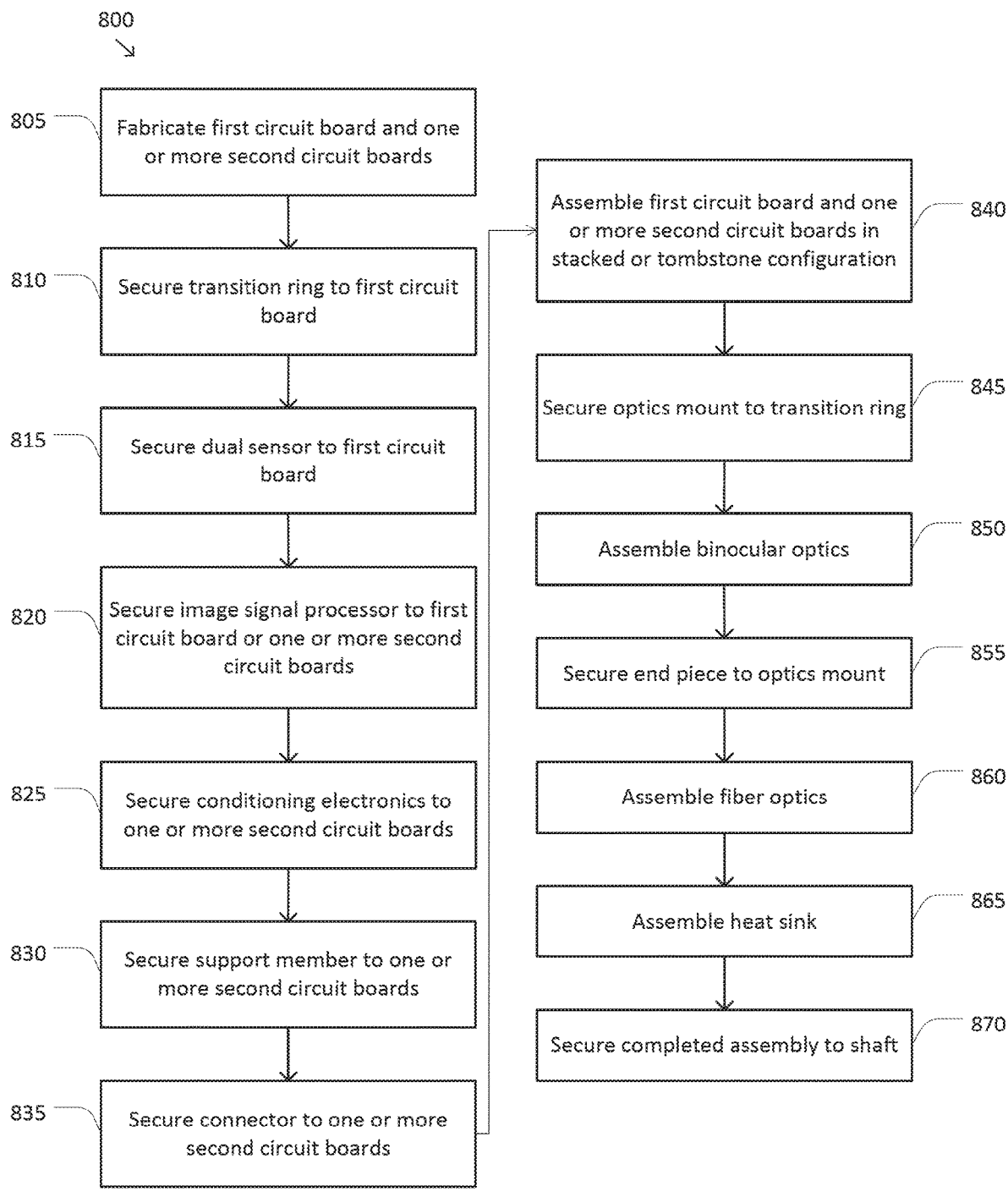
FIG. 8 is a simplified diagram of a method 800 for fabricating a binocular image capture device according to some embodiments.

FIG. 8 is a simplified diagram of a method 800 for fabricating a binocular image capture device according to some embodiments. According to some embodiments consistent with FIGS. 1-7, method 800 may be used to assemble binocular image capture device 400, 500, 600, and/or 700. According to some embodiments, method 800 may be used to assemble the binocular image capture device in a tombstone configuration consistent with FIGS. 5 and/or 6 or in a stacked configuration consistent with FIG. 7. According to some embodiments, the binocular image capture device assembled using method 800 may be very compact, having a diameter of no more than 10 mm and/or an aspect ratio of no more than 10:1. According to some embodiments, the binocular image capture device assembled using method 800 may be compatible with autoclave cleaning. For example, components that are sensitive to moisture may be hermetically sealed to withstand steam treatment, and components that abut one another may have matching coefficients of thermal expansion to withstand thermal cycling.

At a process 805, a first circuit board and one or more second circuit boards are fabricated. According to some embodiments, the first circuit board and/or the one or more second circuit boards may be ceramic circuit boards. When assembling the binocular image capture device in the stacked configuration, the first circuit board and/or the one or more second circuit boards may have approximately the same in-plane shape and/or dimensions. Moreover, the first circuit board and/or the one or more second circuit boards may have may have aligned bonding pads to allow electrical connections between adjacent circuit boards in the stack. Still further, the first circuit board and/or the one or more second circuit boards may have recessed portions to fit electronic components in the stacked configuration.

At a process 810, a transition ring is secured to the first circuit board. According to some embodiments, the transition ring may be a kovar ring with a coefficient of thermal expansion matched to that of ceramic. According to some embodiments, the transition ring may be secured to the first circuit board by brazing.

At a process 815, a dual image sensor is secured to the first circuit board. According to some embodiments, the dual image sensor may be a monolithic image sensor with dual active areas. According to some embodiments, the dual image sensor may have an octagonal shape to increase the fill factor relative to a rectangular shape when placed in a circular tube. According to some embodiments, the dual image sensor may be secured to the first circuit board by wire bonding and/or any other suitable integrated circuit packaging technique.

In some examples, the binocular image capture device may include signal conditioning electronics, such as an image signal processor, electronic devices, and/or the like. At a process 820, an image signal processor is secured to the first circuit board or the one or more second circuit boards. According to some embodiments, the image signal processor may be disposed on the back side of the dual image sensor in a configuration, in which case process 820 merges with process 815 (i.e. securing the dual image sensor and the image signal processor is accomplished during the same steps). According to some embodiments, the image signal processor may be secured to the back side of the first circuit board opposite the dual image sensor. Such embodiments may reduce the distance between the image signal processor and the dual image sensor to facilitate low noise operation. According to some embodiments, the image signal processor may be secured to the one or more second circuit boards (i.e., on a different circuit board than the dual image sensor). Although there is a greater distance between image signal processor and the dual image sensor, such embodiments may reduce the distance between the image signal processor and a heat sink to facilitate heat transfer. According to some embodiments, the image signal processor may be secured to the first circuit board or the one or more second circuit boards by wire bonding and/or any other suitable integrated circuit packaging technique.

At a process 825, electronic devices are secured to the one or more second circuit boards. According to some embodiments, the electronic devices may include one or more resistors, capacitors, inductors, diodes, sensors (e.g., temperature sensors), oscillators, power converters, and/or the like. According to some embodiments, the electronic devices may supply electrical signals to the dual image sensor and/or the image signal processor (e.g., clock signals and/or power signals). According to some embodiments, the electronic devices may condition electrical signals received from the dual image sensor and/or the image signal processor (e.g., the electronic devices may include one or more amplifiers, filters, level shifters, and/or the like for signal conditioning). According to some embodiments, the electronic devices may be secured to the one or more second circuit boards by soldering, wire bonding, and/or the like.

At a process 830, a support member is secured to the one or more second circuit boards. According to some embodiments, the support member may be a copper alloy (e.g., Cu—Mo or Cu—W) to facilitate later connection of a copper heat sink that is not CTE matched with ceramic circuit boards. When assembling the binocular image capture device in the stacked configuration, the support member may be secured to the most proximal circuit board in the stack. When assembling the binocular image capture device in the tombstone configuration, the support member may be secured to the back side of the one or more second circuit boards opposite the electronic devices and/or the image signal processor. According to some embodiments, the support member may be secured to the one or more second circuit boards by brazing.

At a process 835, a connector is secured to the one or more second circuit boards. According to some embodiments, the connector may be configured to transmit captured image data and to receive power and/or control signals. When assembling the binocular image capture device in the stacked configuration, the connector may be secured to the most proximal circuit board in the stack. When assembling the binocular image capture device in the tombstone configuration, the connector may be secured at a proximal end of the one or more second circuit boards. According to some embodiments, the connector may be secured to the one or more second circuit boards by soldering.

At a process 840, the first circuit board and the one or more second circuit boards are assembled in the stacked configuration or the tombstone configuration. When assembling the binocular image capture device in the stacked configuration, electrical contact between the stacked circuit boards is created by aligning the bonding pads and forming conductive contacts using techniques such as ACF, ACP, solder, sintered metal paste, and/or the like. Adhesive may be applied between adjacent circuit boards to improve mechanical integrity and/or heat transfer along the length of the stacked circuit boards. When assembling the binocular image capture device in the tombstone configuration, the one or more second circuit boards are mounted against the back side of the first circuit board and with a perpendicular orientation relative to the first circuit board.

At a process 845, an optics mount is secured to the transition ring. According to some embodiments, the optics mount may include a stainless steel assembly. According to some embodiments, the stainless steel assembly may be formed from a stainless steel alloy with a coefficient of thermal expansion that matches that of ceramic and/or optical glass, such as 17-4 or 440 stainless steel. According to some embodiments, the optic mount may be secured to the transition ring by welding (e.g., laser welding).

At a process 850, binocular optics are assembled. According to some embodiments, the binocular optics are aligned to form a pair of images on the dual image sensor to facilitate 3-dimensional imaging applications. According to some embodiments, the binocular optics include a pair of substantially identical optical assemblies to form each of the pair of images. According to some embodiments, the binocular optics are mounted to the optics mount. In some examples, the binocular optics may be mounted within the optics mount and/or may protrude from the optics mount. According to some embodiments, the binocular optics may include cover glass to cover and/or seal the dual image sensor. According to some embodiments, the cover glass may be glued to a rim of the transition ring and/or the optics mount.

At a process 855, an end piece is secured to the optics mount. According to some embodiments, the end piece may include a stainless steel assembly with similar material properties to the optics mount. According to some embodiments, the end piece may include windows, such as plated sapphire windows. In some examples, the windows may be soldered to the stainless steel assembly of the end piece. According to some embodiments, the end piece may be secured to the optics mount by welding (e.g., laser welding). According to some embodiments, securing the end piece to the optics mount may cause a hermetic seal to form around the binocular optics and/or the dual image sensor. Consequently, process 855 may be performed in a purged environment to prevent moisture and/or contaminants from entering the hermetically sealed volume during the assembly process. For example, process 855 may be performed in an inert gas environment (e.g., nitrogen gas).

At a process 860, fiber optics are assembled. According to some embodiments, the fiber optics may be potted along one or more channels running along an upper and lower portion of the binocular image capture device. Consequently, the potted fiber optics may have a hemicylindrical shape bounded by the curved surface of binocular image capture device on one side and the flat surface of the packed components of binocular image capture device on the other.

At a process 865, a heat sink is assembled. According to some embodiments, the heat sink may include a copper heat pipe. In some examples, the copper heat pipe may be secured to the support member by brazing and/or by welding. According to some embodiments, the heat sink may include a heat sink extension that is coupled to the copper heat pipe by a threaded attachment.

At a process 870, the assembled binocular image capture device of processes 805-865 is secured to a shaft. According to some embodiments, the shaft may be a metal tube that fully or partly encloses the binocular image capture device. According to some embodiments, the shaft may be an 8.8 mm endoscope shaft. According to some embodiments, the shaft is secured by welding (e.g., laser welding) to one or more portions of the binocular image capture device. For example, the shaft may be welded to the end piece. According to some embodiments, thermally conductive paste may be applied between the shaft and the first ceramic board and/or the one or more second ceramic boards to facilitate heat dissipation through the shaft. Such embodiments may be particularly useful when the binocular image capture device does not include a dedicated heat sink (e.g., when processes 830 and/or 865 are omitted from method 800).

Although illustrative embodiments have been shown and described, a wide range of modification, change and substitution is contemplated in the foregoing disclosure and in some instances, some features of the embodiments may be employed without a corresponding use of other features. One of ordinary skill in the art would recognize many variations, alternatives, and modifications. Thus, the scope of the invention should be limited only by the following claims, and it is appropriate that the claims be construed broadly and in a manner consistent with the scope of the embodiments disclosed herein.

What is claimed is:

1. An image capture device comprising:
a plurality of stacked ceramic circuit boards, wherein each ceramic circuit board in the plurality of stacked ceramic circuit boards is parallel and directly coupled to at least one other circuit board in the plurality of stacked ceramic circuit boards;
an image sensor mounted to a first ceramic circuit board of the plurality of stacked ceramic circuit boards;
signal conditioning electronics mounted to one or more of the plurality of stacked ceramic circuit boards and coupled to receive electrical signals generated by the image sensor, wherein the image capture device is enclosed by a shaft, and wherein the plurality of stacked ceramic circuit boards are stacked along a length of the shaft; and
a connector mounted to a second ceramic circuit board among the plurality of stacked ceramic circuit boards, the second ceramic circuit board being on an opposite side of the plurality of stacked ceramic circuit boards from the first ceramic circuit board, wherein the connector is mounted to a side of the second ceramic circuit board that faces away from the first ceramic circuit board.

2. The image capture device of claim 1, further comprising a heat sink coupled to at least one of the plurality of stacked ceramic circuit boards by a support member.

3. The image capture device of claim 2, wherein the support member has a coefficient of thermal expansion that matches that of the at least one of the plurality of stacked ceramic circuit boards.

4. The image capture device of claim 3, wherein the support member comprises a copper alloy.

5. The image capture device of claim 1, wherein the signal conditioning electronics include an image signal processor.

6. The image capture device of claim 5, wherein the image signal processor is disposed on a back side of the image sensor.

7. The image capture device of claim 5, wherein the image signal processor is disposed on a back side of the first ceramic circuit board opposite the image sensor.

8. The image capture device of claim 1, wherein the image sensor is enclosed in a hermetic housing is formed by:
the first ceramic circuit board;
a transition ring secured to the first ceramic circuit board; and
an optics mount secured to the transition ring.

9. The image capture device of claim 8, wherein the transition ring has a coefficient of thermal expansion matched to the first ceramic circuit board.

10. The image capture device of claim 1, wherein one or more of the plurality of stacked ceramic circuit boards have a recessed portion in which to mount the signal conditioning electronics.

11. The image capture device of claim 1, wherein the image sensor is a dual image sensor.

12. The image capture device of claim 1, wherein a thermally conductive paste extends between the shaft and at least one of the plurality of stacked ceramic circuit boards.

13. An image capture device comprising:
a plurality of stacked ceramic circuit boards;
an image sensor mounted to a first ceramic circuit board of the plurality of stacked ceramic circuit boards;
signal conditioning electronics mounted to one or more of the plurality of stacked ceramic circuit boards and coupled to receive electrical signals generated by the image sensor; and
a connector mounted to a second ceramic circuit board among the plurality of stacked ceramic circuit boards, the second ceramic circuit board being on an opposite side of the plurality of stacked ceramic circuit boards from the first ceramic circuit board, wherein the connector is mounted to a side of the second ceramic circuit board that faces away from the first ceramic circuit board.

14. The image capture device of claim 11, further comprising binocular optics projecting a pair of images onto the dual image sensor.

15. A method for assembling an image capture device comprising:
securing an image sensor to a first ceramic circuit board;
securing signal conditioning electronics to a second ceramic circuit board;
securing a connector to a third ceramic circuit board;
stacking the first ceramic circuit board and the second ceramic circuit board parallel and directly to one another to electrically couple the image sensor and the signal conditioning electronics; and
stacking the third ceramic circuit board and the second ceramic circuit board such that the third ceramic circuit board is disposed on an opposite side of the second ceramic circuit board from the first ceramic circuit board, wherein the connector is mounted to a side of the third ceramic circuit board that is opposite a side of the third ceramic circuit board facing the second ceramic circuit board.

16. The method of claim 15 further comprising coupling a heat sink to the third ceramic circuit board with a support member.

17. The method of claim 16, wherein the support member has a coefficient of thermal expansion that matches that of the third ceramic circuit board.

18. The method of claim 15 further comprising sealing the image sensor in an autoclave-tolerant hermetic housing.

19. The method of claim 18 wherein the hermetic housing includes a transition ring having a coefficient of thermal expansion matched to one of the first or second ceramic circuit boards.

* * * * *